US00PP17593P2

(12) United States Plant Patent
Trees

(10) Patent No.: US PP17,593 P2
(45) Date of Patent: Apr. 10, 2007

(54) ***OSTEOSPERMUM* PLANT NAMED 'BALSERDALAV'**

(50) Latin Name: *Osteospermum ecklonis*
Varietal Denomination: Balserdalav

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/283,300

(22) Filed: Nov. 18, 2005

(51) Int. Cl.
*A01H 5/00* (2006.01)

(52) U.S. Cl. ..... Plt./263

(58) Field of Classification Search ..... Plt./263
See application file for complete search history.

(56) References Cited

PUBLICATIONS

European Plant Breeders' Rights application No. 2005/1957 filed Oct. 24, 2005.

*Primary Examiner*—Kent Bell
*Assistant Examiner*—Annette H Para
(74) *Attorney, Agent, or Firm*—Audrey Charles

(57) ABSTRACT

A new and distinct cultivar of *Osteospermum* plant named 'Balserdalav' characterized by its dark lavender-colored ray florets, light purple-colored disc florets, medium green-colored foliage, and upright, mounded growth habit.

1 Drawing Sheet

Latin name of genus and species of plant claimed: *Osteospermum ecklonis*.
Variety denomination: 'Balserdalav'.

BACKGROUND OF THE INVENTION

The present invention relates to a new and distinct cultivar of *Osteospermum* plant botanically known as *Osteospermum ecklonis* and hereinafter referred to by the cultivar name 'Balserdalav'.

The new cultivar originated in a controlled breeding program in Arroyo Grande, Calif. during August 2003. The objective of the breeding program was the development of *Osteospermum* cultivars that are freely flowering with unique inflorescence coloration and a freely branching, compact and upright growth habit.

The female (seed) parent of the new cultivar was 'Balserpurp', U.S. Plant Pat. No. 16,477, characterized by its deep purple-colored ray florets, dark green-colored foliage, and a compact, upright mounded growth habit. The male (pollen) parent of the new cultivar was unknown. The new *Osteospermum* was discovered and selected by the inventor as a single flowering plant within the progeny of the above stated open-pollination during December 2003 in a controlled environment at Arroyo Grande, Calif.

Asexual reproduction of the new cultivar by terminal stem cuttings since December 2003 at Arroyo Grande, Calif. and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balserdalav' as a new and distinct cultivar of *Osteospermum* plant:

1. Dark lavender-colored ray florets and light purple-colored disc florets;
2. Medium green-colored foliage; and
3. Upright, mounded growth habit.

Plants of the new cultivar differ from plants of the female parent primarily in flower and foliage color.

Of the many commercially available *Osteospermum* cultivars known to the inventor, the most similar in comparison to the new cultivar is the female parent 'Balserpurp', U.S. Plant Pat. No. 16,477. However, in side by side comparisons, plants of the new cultivar differ from plants of 'Balserpurp' in the following characteristic: Plants of the new cultivar have a lighter ray floret color than plants of 'Balserpurp'.

BRIEF DESCRIPTION OF THE PHOTOGRAPHS

The accompanying photographs show, as nearly true as it is reasonably possible to make the same in color illustrations of this type, typical inflorescence and foliage characteristics of the new cultivar. Colors in the photographs differ slightly from the color values cited in the detailed description, which accurately describes the colors of 'Balserdalav'. The plants were grown in 10 cm pots for 13 weeks in a greenhouse at West Chicago, Ill.

FIG. 1 illustrates a side view of the overall growth and flowering habit of 'Balserdalav'.

FIG. 2 illustrates a close-up view of an inflorescence of 'Balserdalav' with all of the ray florets open and 2 rows of the disc florets open.

FIG. 3 illustrates a close-up view of an inflorescence of 'Balserdalav' with all of the ray florets open and half of the disc florets open.

DETAILED BOTANICAL DESCRIPTION

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Apr. 27, 2005 between 3:00 p.m. and 4:00 p.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 13 weeks utilizing a soilless growth medium. Greenhouse temperatures were maintained at approximately 60° F. to 75° F. (15° C. to 24° C.) during the day and approximately 45° F. to 55° F. (7° C. to 13° C.) during the night. Greenhouse light levels of 5,000 to 9,000 footcandles were maintained during the day.

Botanical classification: *Osteospermum ecklonis* cultivar Balserdalav.

Parentage:

*Female parent.*—'Balserpurp', U.S. Plant Pat. No. 16,477.

*Male parent.*—Unknown.

Propagation:

*Type cutting.*—Terminal stem.

*Time to initiate roots.*—Approximately 9 to 12 days.

*Time to produce a rooted cutting.*—Approximately 21 to 28 days.

*Root description.*—Fibrous.

*Rooting habit.*—Freely branching.

Plant description:

*Crop time.*—Approximately 10 to 13 weeks from a rooted cutting.

*Growth habit and general appearance.*—Upright, mounded.

*Size.*—Height from soil level to top of plant plane: Approximately 33.9 cm. Height from soil level to top of foliage: Approximately 28.3 cm. Width: Approximately 20.8 cm.

*Branching habit.*—Freely branching. One to two pinches improves basal branching. Approximately 1 main branch per plant and lateral branches forming at every node.

*Branch.*—Strength: Strong. Length from soil level to base of peduncle: Approximately 10.6 cm. Diameter at base: Approximately 8.3 mm. Texture: Glabrous. Color: N144D. Internode length at center of branch: Approximately 8.9 mm.

*Foliage.*—Number of leaves per main branch: Approximately 27. Fragrance: Pungent. Form: Simple. Arrangement: Alternate. Aspect: Right angle or acute angle to stem. Shape: Spatulate. Margin: Dentate. Apex: Acute. Base: Attenuate. Venation pattern: Pinnate. Length of mature leaf: Approximately 8.1 cm. Width of mature leaf: Approximately 4.6 cm. Texture of upper and lower surfaces: Hispid. Color of upper surface of mature foliage: 137A with venation of 145B. Color of lower surface of mature foliage: 137C with venation of 145B. Petiole length: Approximately 1.6 cm. Petiole diameter: Approximately 3.5 mm. Petiole texture: Glabrous. Petiole color: 145B.

Flowering description:

*Flowering habit.*—'Balserdalav' is freely flowering under outdoor growing conditions with substantially continuous blooming from late spring through autumn and year round in greenhouse environment.

*Time to first flower.*—Approximately 15.3 weeks from sticking of unrooted cutting.

*Lastingness of individual bloom.*—Approximately 7 to 10 days.

Inflorescence description:

*Appearance.*—Type: Solitary, composite, persistent. Shape: Round. Aspect: Facing upward. Arrangement: Terminal, held above the foliage, arising from leaf axils. Fragrance: Pungent.

*Quantity per plant.*—Approximately 5.

*Size.*—Diameter: Approximately 6.6 cm. Depth: Approximately 2.2 cm.

*Bud rate of opening.*—Generally takes 3 to 5 days for bud to progress from first color to fully open inflorescence.

*Bud just before opening.*—Quantity per plant: Approximately 3. Shape: Ovate. Length at first color: Approximately 1.6 cm. Diameter at first color: Approximately 1.1 cm. Color: 2B.

*Ray florets.*—Quantity per inflorescence: Approximately: 22. Arrangement: Overlapping. Aspect: Initially at acute angle to disc, becoming nearly perpendicular with some downward turning of apex at maturity. Shape: Oblanceolate. Apex: Emarginate with three tips. Base: Attenuate. Margin: Entire. Length: Approximately 3.4 cm. Diameter: Approximately 9.1 mm. Texture of upper surface: Glabrous. Texture of lower surface: Glabrous with dense pubescence at base. Color of upper surface of fully open ray floret: N78B. Color of lower surface of fully open ray floret: 186D with ribs of 187A.

*Disc.*—Diameter: Approximately 9.7 mm. Depth: Approximately 6.5 mm.

*Receptacle.*—Shape: Round, mounded. Height: Approximately 2.0 mm. Diameter: Approximately 5.3 mm. Color: 154D.

*Disc florets.*—Quantity: Approximately: 72. Arrangement: Acropetally on capitulum. Aspect: Erect. Shape: Tubular. Apex: Five acute tips. Base: Attenuate, fused. Margin: Entire. Length: Approximately 7.9 mm. Diameter at apex: Approximately 2.4 mm. Diameter at base: Approximately 1.0 mm. Texture of upper or inner surface: Glabrous. Texture of lower or outer surface: Pubescent. Color of inner and outer surfaces: 75B with tips of 83B.

*Phyllaries.*—Quantity per inflorescence: 23. Arrangement: In one whorl. Shape: Linear to lanceolate. Aspect: Acute angle to stem. Apex: Acute. Base: Truncate. Margin: Entire. Length: Approximately 9.3 mm. Width: Approximately 2.2 mm. Texture of upper or inner surface: Glabrous. Texture of lower or outer surface: Pubescent. Color of upper or inner surface: 144A in center with 150C along margins. Color of lower or outer surface: 144B in center with 150C along margins.

*Peduncle.*—Strength: Strong. Aspect: Erect. Length: Approximately 7.8 cm. Diameter: Approximately 1.6 mm. Texture: Hispid. Color: 144B.

*Reproductive organs.*—Androecium, on disc florets only: Stamen quantity: 5 per floret, fused around the style. Stamen length: Approximately 6.0 mm. Anther shape: Linear. Anther length: Approximately 3.0 mm. Anther color: N187B with N187A at apex. Pollen amount: Abundant. Pollen color 17B. Gynoecium, on disc and ray florets: Pistil quantity: One per floret. Pistil length: Approximately 9.0 mm. Stigma shape: Two-parted. Stigma length: Approximately 0.8 mm. Stigma color: N186A. Style length: Approximately 5.5 mm. Style color: 4D. Ovary length: Approximately 2.0 mm. Ovary texture: Glabrous. Ovary color: 4D.

Seed and fruit production: Neither seed nor fruit production has been observed.

Disease and pest resistance: Resistance to pathogens and pests common to *Osteospermum* has not been observed.

What is claimed is:

1. A new and distinct cultivar of *Osteospermum* plant named 'Balserdalav', substantially as herein shown and described.

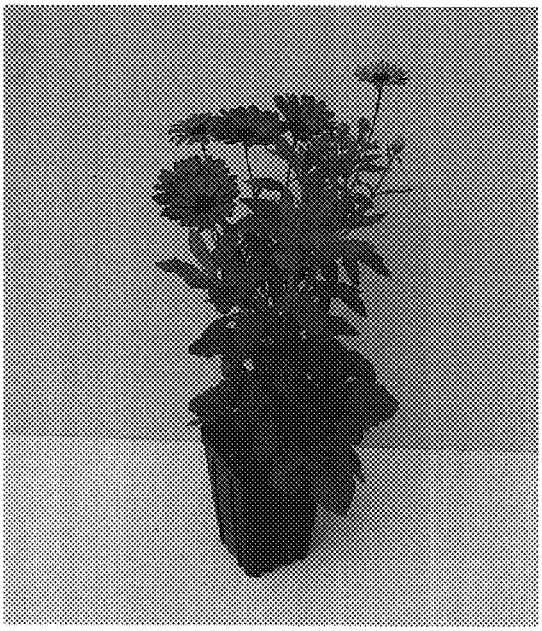
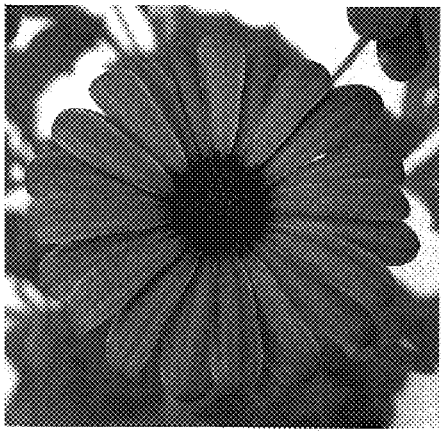
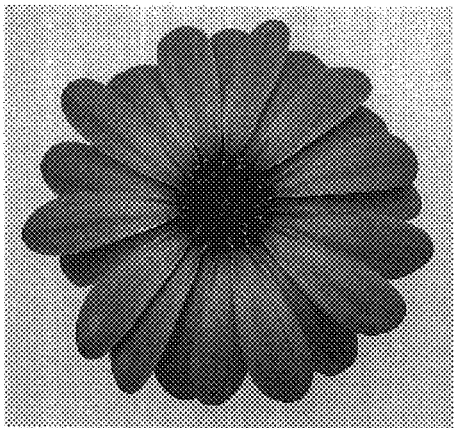

* * * * *